United States Patent [19]

Brown et al.

[11] Patent Number: 4,529,581

[45] Date of Patent: Jul. 16, 1985

[54] DETERMINING POTENCY OF STREPTOCOCCAL PREPARATIONS

[75] Inventors: Karen K. Brown, Kansas City, Mo.; Sharon A. Bryant, Shawnee, Kans.

[73] Assignee: Miles Laboratories, Inc., Elkhart, Ind.

[21] Appl. No.: 454,906

[22] Filed: Dec. 30, 1982

[51] Int. Cl.³ .................... A61K 49/00; G01N 33/48; G01N 33/54
[52] U.S. Cl. .......................................... 424/9; 424/88; 436/536; 436/538; 436/543
[58] Field of Search .............. 436/537, 538, 536, 543; 424/9, 88

[56]     References Cited
    U.S. PATENT DOCUMENTS
3,940,475  2/1976  Gross ................................. 436/537

FOREIGN PATENT DOCUMENTS
0623865  9/1978  U.S.S.R. .................................. 424/9

OTHER PUBLICATIONS

Maggio, V. Enzyme-Immunoassay, CRC Press Inc., Florida, 1980, pp. 168-170.
Lancefield, J. Exp. Med., 106 (1957) 525-544.
Lancefield, J. Exp. Med., 67 (1938) 25-40.

Primary Examiner—Christine M. Nucker
Attorney, Agent, or Firm—James A. Giblin

[57]     ABSTRACT

Antigenicity of streptococcal preparations useful for inducing anti-streptococcal immunity in animals can be determined using a combining power technique. Method involves incubating serial dilutions of the antigen preparation with known amounts of anti-streptococcal antiserum, thereby lessening, in serial manner, the combining power of the antiserum. The serial reaction products are then incubated with serial dilutions of streptococcal preparations having known activity and the effects of the serial reaction products on such activity are then determined by in vivo means. Those determinations can be related to a standard for determining potency of the streptococcal preparation. Assay technique is especially useful in determining potency of *Streptococcus equi* bacterins or bacterin derivatives.

6 Claims, 2 Drawing Figures

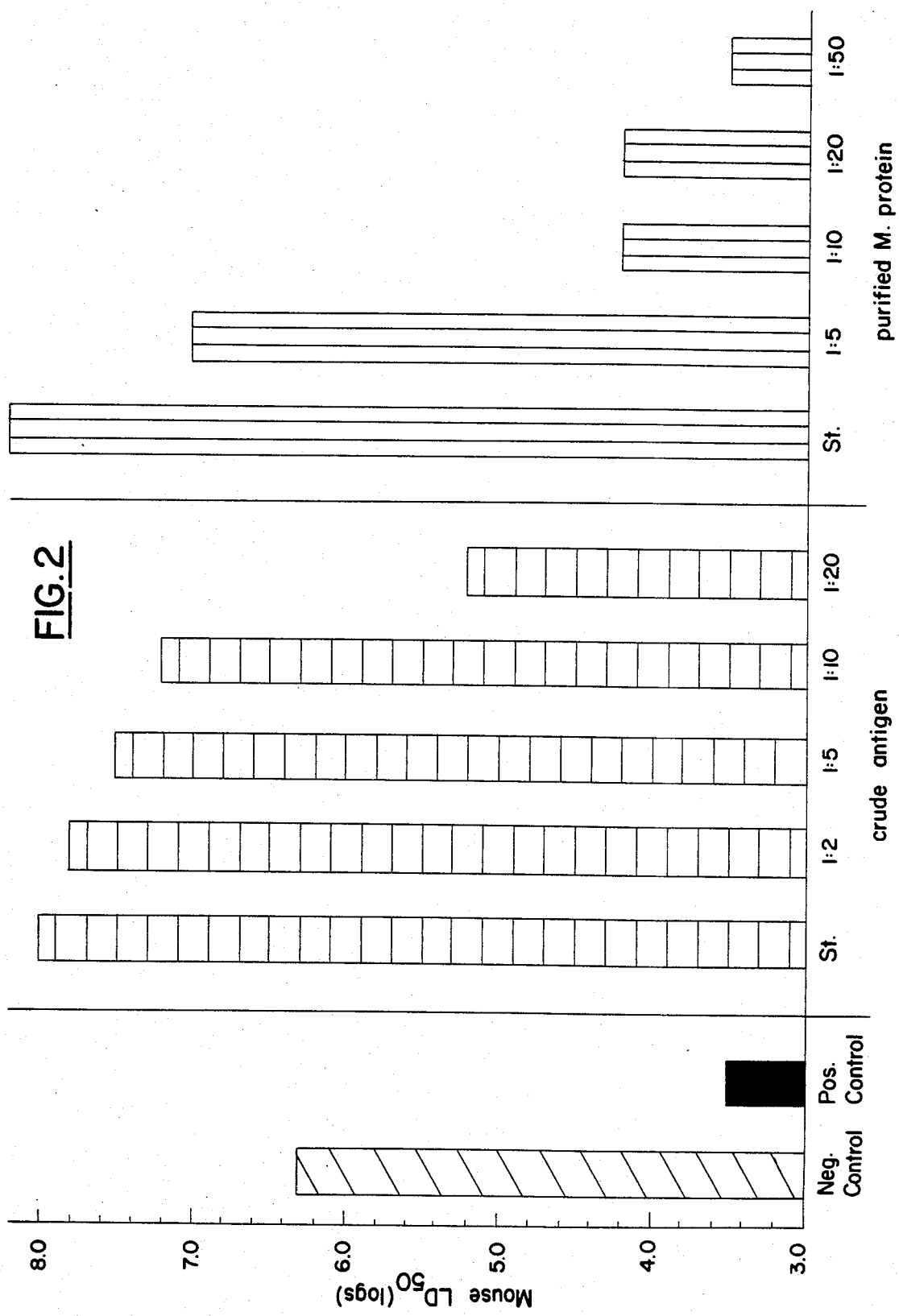

DETERMINING POTENCY OF STREPTOCOCCAL PREPARATIONS

RELATED APPLICATION

Application Ser. No. 454,908, filed of even date herewith in the names of K. K. Brown and S. A. Bryant and entitled Titration of Group C Streptococcal Antibody.

BACKGROUND OF THE INVENTION

1. Field

This disclosure is concerned generally with a biological assay useful for determining the potency of antigenic preparations and specifically with determining the antigenicity or potency of preparations useful for immunizing animals against bacteria of the genus Streptococcus, especially group C streptococcal organisms such as *Streptococcus equi*.

2. Prior Art

Organisms of the genus Streptococcus include a variety of nonmotile, chiefly parasitic, gram-positive bacteria that divide only in one plane, occur in pairs or chains, but not packets, and include important pathogens of man and domestic animals. The streptococcal genus has been divided into eight distinct groups labeled A, B, C, D, F, G, H, and K. It is known that Group A and B human *Streptococci* have an affinity for heart muscle causing rheumatic fever, endocarditis, and sometimes death. A Group C organism, *Streptococcus equi*, is the causitive agent of a severe respiratory disease of horses referred to as "Strangles". The disease is endemic in most parts of the world and epidemic in the United States. Race and show horses are particularly susceptible to repeated infections due to the stress of travel and exposure to new contacts. The disease begins with a mucopurulent nasal discharge, temperatures of 103°–106° F., and severe inflammation of the upper respiratory mucosa. It finally progresses to lymphadenitis and abscess formation which is sometimes severe enough to restrict air intake and cause suffocation of the animal. Strangles results in extensive loss of condition (loss of weight) as it often runs a course of 4–6 weeks. The single strain of *Streptococcus equi* (a Lancefield Type C Strep.) is responsible for this disease worldwide. See for example, Bergy's Manual of Determinitive Bacteriology (8th Edition), p. 498 (1974). The only other known susceptible animal is the mouse.

Because of the debilitating and in some cases lethal effects of streptococcal infections in man and other animals, attempts have been made over the years to prepare streptococcal bacterins or bacterin-like preparations which could be used for active immunization purposes. Unfortunately, some streptococcal preparations tend to be very reactive and it has been noted that human streptococcal "vaccines" have stimulated heart muscle reactions while *Strep. equi* preparations, in live or inactivated forms, have been noted for their affinity for dermal tissue, producing severe swelling at the injection site. These known reactivities have tended to discourage the development and/or commercial use of immunizing streptococcal products for man and other animals. *Strep. equi* ("M-protein extraction") preparations are available and have been described in U.S. Pat. No. 3,793,150 and U.S. Pat. No. 3,852,420. The purification of such M-like proteins is also described in an article by J. B. Woolcock, Infection & Immunity, July, 1974, p. 116–122. Although there does exist a whole culture, chemically inactivated, *Strep. equi* preparation (Ft. Dodge Corp.), the product appears to provide only minimal reduction in Strangles disease symptoms and produces significant swellings and stiffness due to the high reactivity of that bacterin. This has resulted in relatively modest acceptance of the product.

In efforts to prepare a non-reactive and efficacious streptococcal vaccine in general and a *Streptococcus equi* vaccine in particular, it would be highly desirable to have available an accurate assay for determining the potency of the final streptococcal preparation since a commercial streptococcal preparation should be, ideally, not only non-reactive, but it should also have a reliable and quantifiable potency or antigenicity. In our efforts to prepare a *Streptococcus equi* vaccine, we soon became aware that there was no laboratory method (as opposed to in vivo testing in horses per se) for determining antigenicity. Thus, it became quite important to devise a reliable method, other than simple horse challenge, to quantitate immunogenicity of a given preparation. Quite surprisingly, we found that such a method is possible, thus obviating the use of horses for routine antigen potency testing. Although our indirect method of antigen quantitation has been found especially useful in evaluating a specific Group C streptococcal antigen preparation derived from *Strep. equi*, it is thought that our method is applicable for determining the potency of all Streptococcal antigen preparations. Details of our potency determination method are disclosed below.

BRIEF DESCRIPTION OF THE FIGURES

FIG. 2 is a graph showing the results obtained using our combining power test to determine the antigenicity of positive and negative controls for a *Streptococcus equi* preparation as well as the effects of dilution on the antigenicity of both a crude heated antigen preparation and a purified M-protein obtained from a *Strep. equi* extraction.

SUMMARY OF THE INVENTION

Figure 1:
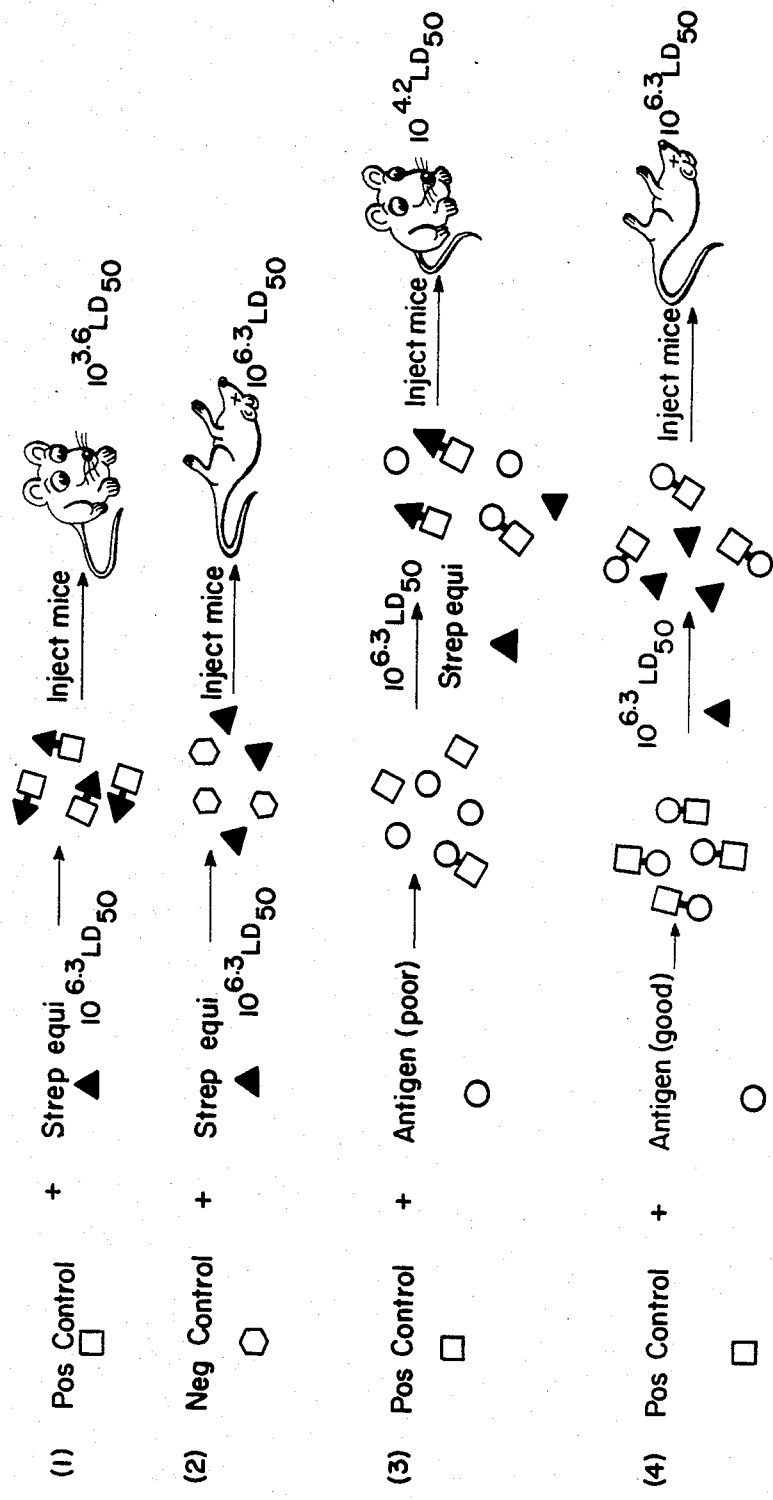
FIG. 1 illustrates in schematic form the principles of our streptococcal antigen combining power assay, as applied in vivo, using mice. The $LD_{50}$ values of FIG. 1 are taken from the results illustrated in FIG. 2.

Our method of determining the potency of a streptococcal antigenic preparation useful for inducing streptococcal immunity in animals comprises several general steps. In the first step, serial dilutions are made of the streptococcal preparation of unknown potency or antigenicity. These serial dilutions are then incubated with separate and equal amounts of an antiserum having a known quantity of antibodies to the streptococcal antigen. The incubation is under conditions sufficient to assure that immunochemical (antigen-antibody) complexes form. This step has the effect of reducing the known combining power of the antibodies for the varying amounts of unknown antigen in the serial dilutions. The reduction in antibody combining power will be in direct proportion to the respective amounts of antigen in the serial dilutions. The next step involves measuring these respective reductions in combining power and relating those measurements to a standard which in turn can be related to the potency of the original antigen preparation. This is accomplished by mixing the separate reaction products (each having a combining power reduction related to the serial dilution of the unknown antigen with which it has been incubated) with an amount of the active streptococcal organism known to be lethal in a given in vivo test application (e.g. $LD_{50}$ in mice). Since the lethality of the active streptococcal preparations will be affected by the amount of combining power remaining in the antibody-antigen mixture after the first incubation step, and since the remaining combining power will be directly related to the potency of the original antigen preparation, observations on the changes in the lethality of the second incubation product can be related via a standard to antigen potency. This lethality determination can be made by inoculating separate groups of a susceptible animal (e.g. mice) with the reaction products of the second incubation and determining the $LD_{50}$ and relating this determination to negative and positive standards to determine the unknown antigen potency.

In the above case, the antigen potency determinations can be determined under laboratory conditions, thus greatly simplifying the routine potency testing of streptococcal antigen preparations. This has the practical effect of accelerating the discovery of safe, effective and, very importantly, non-reactive immunogenic streptococcal preparations for both man and other animals.

SPECIFIC EMBODIMENTS

Our discovery of an indirect method of determining potency of streptococcal preparations is based on our attempts to prepare a non-reactive *Strep. equi* preparation which could be used to immunize horses against Strangles disease. As a result of our work, we were able to obtain specific information about the protective antigen (using immunodiffusion and electrophoresis techniques to identify and quantitate the antigen). We have determined that an M-like protein is produced by *Strep. equi* and this appears to be the protective antigen. The M-protein is heat extractable and can be produced, for example, as shown in the patents and literature cited above.

Such a streptococcal M-like antigen preparation was used in the Examples below to show how the combining power test could be used using an in vivo technique (mice $LD_{50}$). The specific steps involved in our test are illustrated in FIG. 1. As can be seen from (l) of FIG. 1, when a positive control having a known amount of antibody is mixed with a lethal dose of active *Strep. equi* in mice ($10^{6.3}$ $LD_{50}$), the antibody of the control will combine with at least a portion of the lethal dose of the *Strep. equi,* thus reducing its lethality (in this case, to $10^{3.6}$ $LD_{50}$). In the case of the negative control at (2), however, there is no antibody to the *Strep. equi* antigen and, hence, no combining with the *Strep. equi* to reduce its lethality (which remains at $10^{6.3}$ $LD_{50}$). The use of the combining power test to determine antigen potency can be seen in (3) and (4). In (3), an antigen preparation of low potency (antigen poor) is incubated with the positive control and the products of this incubation are then incubated with a lethal dose of *Strep. equi.* As can be seen, since the test preparation had a low potency in (3), the remaining combining power of the positive control antibodies was sufficient to reduce to $10^{4.2}$ $LD_{50}$ the lethality of a $10^{6.3}$ $LD_{50}$ preparation. In the case of a high potency antigen preparation (antigen good), the combining power of the positive control is taken up (reduced) by the high potency antigen preparation. Hence, when a lethal dose is incubated with the combination of high potency antigen and the positive control, as in (4), lethality is not reduced. As can be appreciated, variations in observations of lethality between very weak and very potent antigen preparations can be used to establish a standard against which unknown potencies can be determined as illustrated in FIG. 2, described below. Our test is illustrated further in the Example below.

EXAMPLE (in vivo mice $LD_{50}$ test)

The potency of an unknown *Streptococcus equi* preparation was determined on an in vivo basis as follows:

1. A known positive *S. equi* antiserum (horse, rabbit or mouse) is mixed with equal volumes of unknown antigen dilutions for a period of time (e.g. 5 ml quantities of antiserum and antigen dilutions are mixed and then allowed to incubate at 4° C. for 1 hour).
2. Antibody combines with antigen if specific sites are present. The preparations are then centrifuged to remove antigen-antibody complexes to prevent interference in the test.
3. The remaining soluble antibodies are incubated with a known lethal mouse challenge of *Strep. equi* (e.g. $LD_{50}$ 7.0–8.0 diluted in Todd Hewitt Broth) to neutralize all or a portion of the lethal challenge, the extent of the neutralization being dependent on the amount of soluble antibody present.
4. The unneutralized portion of the lethal challenges are then titrated in mice.
   a. If positive antiserum has been bound by antigen, it cannot neutralize challenge and challenge will be lethal.
   b. If positive antiserum is only partially bound (poor antigen preparation) there will be partial reduction in the lethal challenge.
   c. If positive antiserum is unbound, there will be reduction in the lethal challenge equivalent to the positive serum control.
   d. A negative serum control or antigen control and a positive antiserum control are also run.
   e. Results are recorded simply as Mouse $LD_{50}$. The higher the $LD_{50}$, the more potent the antigen. In our Examples, the $LD_{50}$s were determined by the Reed Muench Method.

This combining power test has been found to correlate directly with horse protection after vaccination. A mouse $LD_{50} \geqq 6.0$ appears adequate for host efficacy. The results obtained using both positive and negative controls are shown in FIG. 2. Also shown in FIG. 2 are the effects of dilution on the $LD_{50}$ in mice of both crude antigen and a purified M-protein preparation. As can be appreciated, the test of this disclosure includes a negative control. The negative control in the test will indicate the complete lack of antibody present to neutralize the *S. equi* cultures. Therefore, any antigen preparation showing a $LD_{50}$ equal to or greater than the negative control would be considered potent. This is shown, for example, in FIG. 2 where it can be seen that the crude antigen preparation (middle bar graph) is potent up to and including a dilution of 1:10 whereas the more pure preparation (the purified M-protein of the right bar graph) is potent only up to and including a dilution of 1:5.

It should be understood that the above example of our test is merely illustrative. Accordingly, it is intended that the scope of this disclosure should be limited only by the following claims.

We claim:

1. A method of determining the potency of a Group C streptococcal antigen preparation, the method comprising the steps of:
   (a) preparing serial dilutions of the unknown antigen preparation;
   (b) incubating the serial dilutions of step (a) with separate and equal amounts of an antiserum having a known quanitity of antibodies to the antigen, to form a reaction mixture, the incubation being under conditions sufficient to form first immunochemical reaction complexes with at least some of the antibodies;
   (c) removing the first immunochemical reaction complexes of step (b) and then incubating the remaining uncomplexed antibodies in the reaction mixture of step (b) with separate, equal and known amounts of the active streptococcal preparation, the incubations being under conditions sufficient to form second immunochemical complexes and remaining reaction products comprising uncomplexed and active streptococcal organisms;
   (d) observing via in vivo means in mice the effects of the remaining reactive products of step (c); and
   (e) relating the observations of step (d) to a standard to determine the potency of the antigen preparation.

2. The method of claim 1 wherein the removal is via centrifugation means.

3. The method of claim 1 wherein the preparation is an equine streptococcal preparation.

4. The method of claim 3 wherein the preparation is a *Streptococcus equi* preparation.

5. The method of claim 1 wherein the observations of step (d) comprise inoculating separate groups of mice with the remaining reaction products of step (c).

6. The method of claim 5 wherein the susceptible animals are mice and the observation step includes determining the $LD_{50}$ of the remaining reaction products for the group of mice.

* * * * *